(12) United States Patent
Eversull et al.

(10) Patent No.: US 9,393,400 B2
(45) Date of Patent: Jul. 19, 2016

(54) COUPLING FOR A MEDICAL DELIVERY DEVICE

(75) Inventors: Christian S. Eversull, Palo Alto, CA (US); Stephen A. Leeflang, Sunnyvale, CA (US); Matthias Wenzel, Berlin (DE)

(73) Assignee: BIOTRONIK SE & CO KG, Berlin (DE)

( * ) Notice: Subject to any disclaimer, the term of this patent is extended or adjusted under 35 U.S.C. 154(b) by 979 days.

(21) Appl. No.: 13/015,097

(22) Filed: Jan. 27, 2011

(65) Prior Publication Data

US 2011/0270268 A1    Nov. 3, 2011

Related U.S. Application Data

(60) Provisional application No. 61/328,870, filed on Apr. 28, 2010.

(51) Int. Cl.
*A61B 19/00* (2006.01)
*A61M 39/10* (2006.01)
*A61M 25/00* (2006.01)
*A61M 25/06* (2006.01)

(52) U.S. Cl.
CPC ........... *A61M 39/10* (2013.01); *A61M 25/0097* (2013.01); *A61M 25/0668* (2013.01); *A61M 2039/1027* (2013.01); *A61M 2039/1033* (2013.01)

(58) Field of Classification Search
CPC ............ A61M 39/10; A61M 25/0668; A61M 2039/1027; A61M 2039/1061; A61M 2039/1033
USPC ............................ 604/160, 240–241; 606/129
See application file for complete search history.

(56) References Cited

U.S. PATENT DOCUMENTS

| 5,947,954 | A | * | 9/1999 | Bonaldo | 604/533 |
| 6,159,198 | A | | 12/2000 | Gardeski et al. | |
| 2001/0049499 | A1 | * | 12/2001 | Lui et al. | 604/164.05 |
| 2004/0267202 | A1 | * | 12/2004 | Potter | A61M 39/06 604/158 |
| 2010/0094225 | A1 | | 4/2010 | Hastings et al. | |

FOREIGN PATENT DOCUMENTS

WO    0102047    1/2001

OTHER PUBLICATIONS

European Search Report and Annex to the European Search Report on European Patent Application No. EP 11 16 1561, dated Jul. 16, 2012 (9 pages).

* cited by examiner

*Primary Examiner* — Katherine Rodjom
(74) *Attorney, Agent, or Firm* — Buchanan Ingersoll & Rooney PC

(57) ABSTRACT

The present disclosure relates to a coupling, in particular a hub (2 *a-i*), with a base body (23 *a-i*) having a proximal end (24 *a-i*), embodied as a connecting region (25 *a-i*) for an applicator (26 *a-i*), and a distal end (27 *a-i*), embodied as connecting region (28 *a-i*) for a delivery device (29 *a-i*) with a tubular member (30 *a-i*) for delivering a medical device (31 *a*-1) into a part of an animal or human body, and having a recess (9 *a-i*) extending between the proximal end (24 *a-i*) and the distal end (27 *a-i*). It is provided that the recess (9 *a-i*) is positioned eccentrically from an outer diameter (20 *a-i*) of the base body (23 *a-i*) and a central axis (18 *a-i*) of the recess (9 *a-i*) is nonparallel in respect to a central axis (32 *a-i*) of the outer diameter (20 *a-i*) of the base body (23 *a-i*).

12 Claims, 15 Drawing Sheets

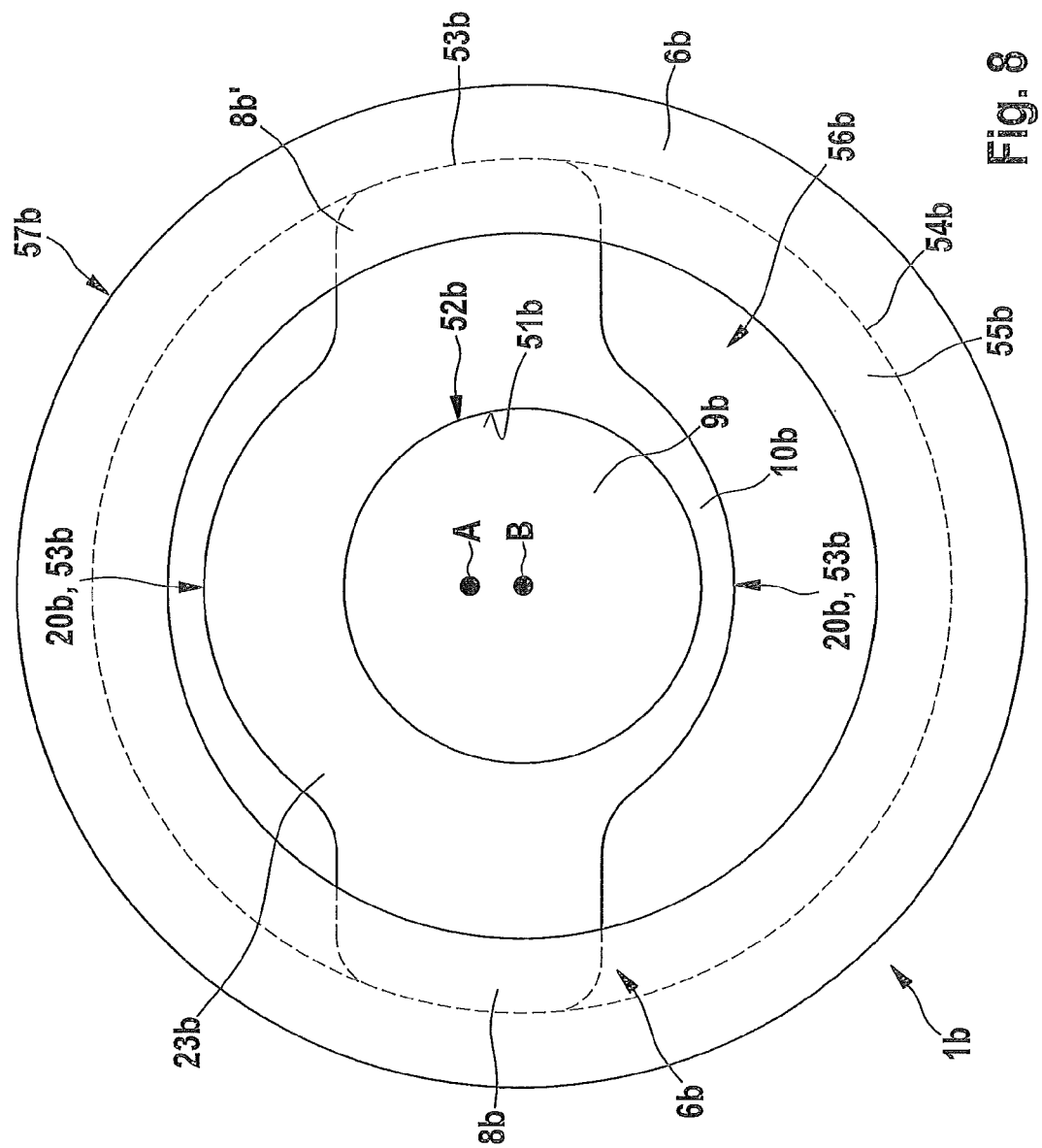

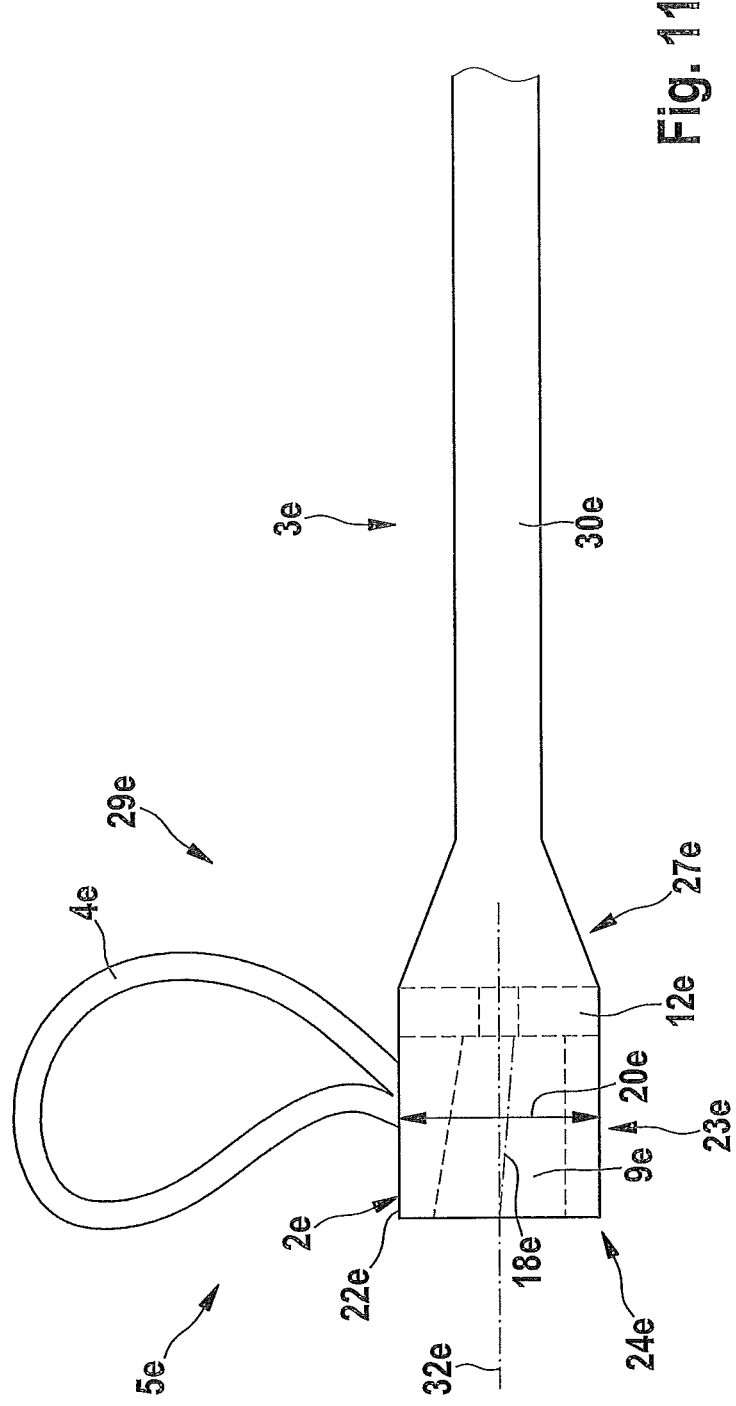

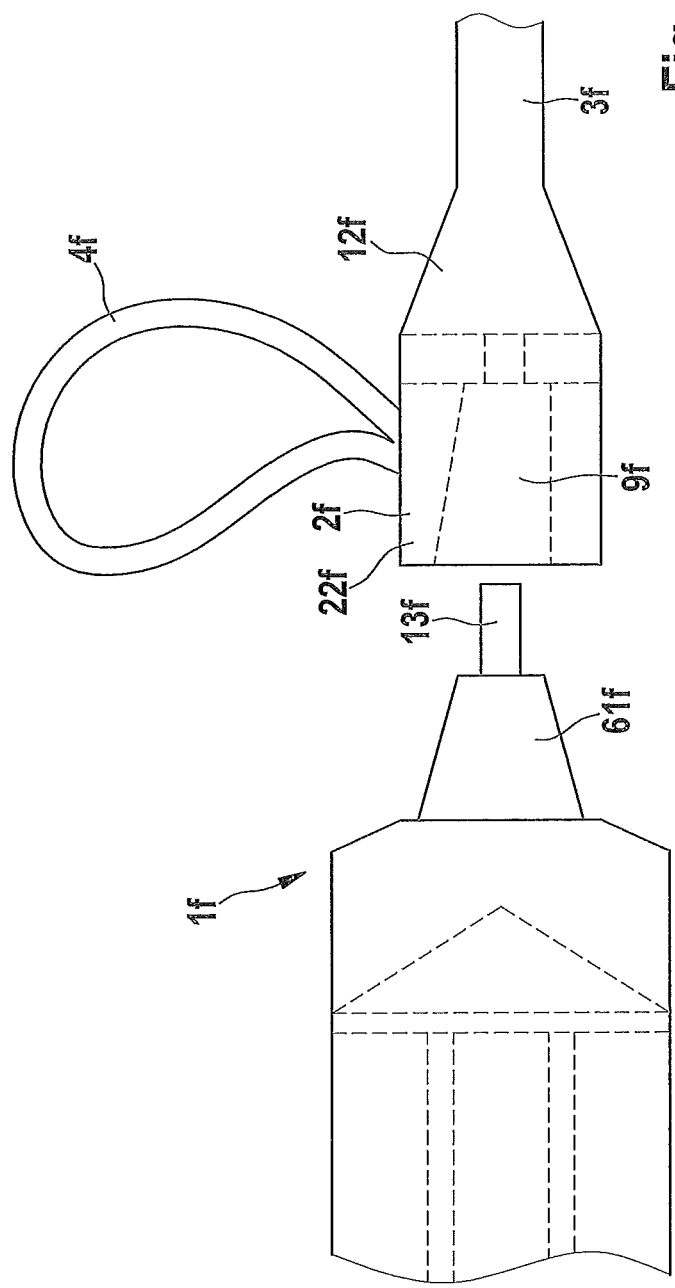

COUPLING FOR A MEDICAL DELIVERY DEVICE

CROSS-REFERENCE TO RELATED APPLICATIONS

This patent application claims the benefit of U.S. Provisional Patent Application Ser. No. 61/328,870 entitled "Coupling", filed on Apr. 28, 2010, the entire disclosure of which is hereby incorporated by reference herein.

FIELD OF THE INVENTION

The present disclosure relates to a coupling for a medical delivery device and, more particularly, to a coupling for a medical delivery device having improved slittability.

BACKGROUND OF THE INVENTION

When performing vascular procedures, it may be desirable to deliver diagnostic and/or therapeutic agents into the body. It may be further desirable to deliver such agents while manipulating the position of a delivery device within the body. For example, in the setting of cardiac lead delivery, it may be desirable to simultaneously infuse radiocontrast through a delivery sheath while manipulating the sheath within the chambers of the heart. It may be further desirable to subsequently deliver a pacing lead to the heart through the delivery sheath and then remove the delivery sheath to leave the pacing lead in place. As a specific example, a delivery sheath may be introduced into the right atrium of the heart. The position of the delivery sheath within the heart may be manipulated and radiocontrast infused in order to identify and/or cannulate the coronary sinus. Subsequently, the position of the delivery sheath within the coronary sinus may be manipulated and radiocontrast infused in order to identify and/or cannulate a coronary venous tributary to the coronary sinus. Subsequently, a left ventricular pacing lead may be delivered to the venous tributary through the delivery sheath, after which the delivery sheath may be split or slit and than removed leaving the pacing lead in place. Such delivery devices are known, for example, from U.S. Pat. No. 6,159,198 and U.S. Publication No. 2007/0293845, the disclosures of which are hereby incorporated by reference herein.

A problem that arises is that the devices could have problems with easy slittability or splittability of the delivery device due to constructive properties of the device.

A problem addressed by this patent application is that of creating a coupling for a delivery device which has a slitting side with an improved slittability.

The present invention is directed toward overcoming one or more of the above-identified problems.

SUMMARY OF THE INVENTION

The problem according to the present disclosure is solved by the features of claim 1. Favorable embodiments and advantages of the present disclosure result from the further claims, the drawings, and the description.

The present disclosure is directed to a coupling, in particular a hub, with a base body having a proximal end, embodied as a connecting region for an applicator, and a distal end, embodied as connecting region for a delivery device with a tubular member for delivering a medical device into a part of an animal or human body, and having a recess located/extending between the proximal end and the distal end.

It is provided that the recess is positioned eccentrically from an outer diameter of the base body and a central axis of the recess is nonparallel with respect to a central axis of the outer diameter of the base body. The embodiment according to the present disclosure provides a coupling which could be easily removed after placement of the medical device at an implantation site. Furthermore, the coupling could be constructed robustly and thus reliable.

A "coupling" as used herein is intended to mean, in particular, a structure by which at least two components of an apparatus can be connected, wherein the apparatus is intended for delivering and/or extracting an implant, an instrument, a medical device and/or an agent during a medical procedure, like, for example, a vascular procedure, into or from an animal's and/or human's body part, cavity, recess, vessel, organ, and/or other lumen, like, for example, a gastrointestinal tract, a urogenital tract, a reproductive tract, a respiratory tract, a lymphatic system, and particularly a vasculature. The coupling process could be irreversible or preferably reversible. Moreover, the connection of the coupling with a component of the apparatus could be performed by any suitable connecting process by, for example, an adhesive bond, a friction fit, a snap fit, a form and/or force closure, like glueing, welding, crimping, screwing, knotting and/or any other process being feasible for a person skilled in the art.

In this context, a "component" as used herein is intended to mean, in particular, an applicator, like an adapter, a syringe, a medical tube or a valve, or a delivery device, like a delivery shaft, a guide catheter, and/or other tubular member, to deliver a medical device, like a lead, a catheter and/or an electrode to a target location. However, any other component that appears reasonable to a person skilled in the art would also be feasible and is considered within the spirit and scope of the present invention.

Further, a "tubular member" as used herein is intended to mean, particularly, a structure with at least one tube.

Furthermore, a "base body" as used herein in this context is intended to mean, in particular, a structure that substantially imparts a shape and/or form of the coupling. It is preferably manufactured out of plastic, but other materials are also contemplated. Basically, it would also be feasible, however, for the base body to be composed at least partially of a biodegradable material.

In this context, a "proximal end" as used herein is intended to mean, in particular, an end of the coupling or the base body, respectively, which, in the state of the medical procedure, is oriented towards an operator.

Thus, a "distal end" as used herein is intended to mean, in particular, an end of the coupling or the base body, respectively, which, in the state of the medical procedure, is oriented away from the operator and/or toward the part of the animal's and/or human's body where the medical procedure takes place.

In this case, a "connecting region" as used herein defines, in particular, a region, where a connection with another component takes, took or can take place and/or which has or where at least a connecting means, like, for example, an electrical connector, a screw, a recesses, a groove, a ridge, a detent, a lug, a protrusion, a thread and/or any other means which is feasible for a person skilled in the art, is located and/or formed. Preferably, the connecting region is adapted to accept a male Luer fitting.

Furthermore, a "recess" as used herein in this context is intended to mean, in particular, a cavity, a hole and/or, in particular, a through hole.

The phrase "extending between the proximal end and the distal end" as used herein is intended to mean, in particular, that the recess extends along an axial extension of the base body.

In addition, an "outer diameter" of the base body as used herein is intended to mean, in particular, the greatest extension of the base body perpendicular to the central axis of the base body in an area or region of the base body located between the connecting regions at the proximal and the distal ends, and thus the area has no connecting means. As a result, the radial width of a connecting means does not contribute to the outer diameter of the base body.

Advantageously, a coupling is provided with a base body which has at least a weak spot which extends at least in an axial direction of the base body and is intended for splitting or slitting of the base body. In this context a "weak spot" as used herein is intended to mean, in particular, a thinned wall segment, a score line, a groove and/or other means to facilitate splitting or slitting. Other possibilities that are feasible are all embodiments that appear suitable to a person skilled in the art, such as a section of the base body manufactured of a material with less resilience and/or resistibility as the residual part of the base body. The weak spot generally extends along the whole axial extension of the base body. Moreover, the weak spot generally extends preferably in circumferential direction of the base body at least matched to a dimension and/or a width, respectively, of a tool for splitting or slitting, like, for example, a cutter. By means of the weak spot the opening of the base body and therefore, the removal of the delivery device could be performed easily and without disturbance of the location of the delivered medical device.

Moreover, it is provided that the weak spot is embodied as a thin wall segment having a uniform width in least an axial direction of the base body. Possible is also a uniform width in circumferential direction as described below. However, for the scope of the present disclosure, for the slittability of the hub, only the uniform width in axial direction is essential. Preferably, the thin wall segment extends uniformly in circumferential direction of the base body with a width that is at least matched to the dimension and/or the width, respectively, of the tool for splitting or slitting. Moreover, the width of the connected downstream delivery shaft of the delivery device is matched and/or preferably equal to the width of the thin wall segment.

A "thin wall segment" as used herein refers, in particular, to a segment or first segment of the base body which extends along a part of the circumference of the base body and partly abuts the recess and which is at least 1.2 times to 10 times thinner, preferably 1.5 times to 5 times thinner, and particularly advantageously 2 times to 3 times thinner than another, second segment of the base body, which extends along a part of the circumference of the base body, partly abuts the recess and is no part of a connection means.

The term "uniform" as used herein should be understood as homogeneous, even and/or similar. Minimal deviations in the uniformity, such as an irregularity about ±1% to 5% from the width of the thin wall segment, do not alter the scope of the definition. Due to the thin wall segment, the splitting and/or slitting can be realized without complications and especially gentle for structures and/or tissue located in proximity to the delivery device.

Helpfully, with respect to the thin wall segment a thicker wall segment is positioned diametrical opposite to the thin wall segment and wherein the thicker wall segment provides a structural support for the base body. The width of the thicker wall segment preferably increases in a radial direction of the recess from the proximal to the distal end of the base body.

The thin and the thicker wall segments and/or the first and the second segments, respectively, could have the same circumferential length or different circumferential lengths. A slightly offset positioning of the thin and the thicker wall segments towards each other still falls within the spirit and scope of the present invention, as defined by the appended claims. The embodiment according to the present disclosure provides preferably a solid coupling which has only minimal risk of collapsing during the medical procedure.

Furthermore, it is advantageous when the connecting region at the proximal end of the base body has at least one Luer fitting. In this context, a "Luer fitting" as used herein is intended to mean, in particular, a male and preferably a female Luer fitting. It is therefore usefully possible to easily connect the coupling with devices embodied with state of the art Luer locks. As a result, the coupling can be advantageously used with a great range of devices.

In a further embodiment of the present disclosure, the connecting region at the proximal end of the base body has at least one tab extending in a circumferential direction of the base body. The tab could extend along an inner circumference and/or an outer circumference of the base body. Moreover, the tab could extend over the whole inner and/or outer circumference of the base body, via which a robust snap fitting connection with an upstream component, like, for example, the applicator, could be achieved.

It is furthermore provided that the connecting region at the proximal end of the base body has at least one tab extending over a part of the outer circumference of the base body. The tab is intended for engaging a threaded Luer lock fitting, specifically a male Luer fitting. Due to this mechanism, the connection between the coupling and the upstream component could be realised both reversibly and securely.

Furthermore, the connecting region at the proximal end of the base body has at least two tabs, which are positioned diametrical towards each other and are extending over a part of the outer circumference of the base body. Preferably, the tabs are intended to engage a threaded Luer lock fitting, specifically a male Luer fitting. Moreover, the tabs could have the same circumferential length or different lengths. A slight offset in positioning of the two tabs towards each other still falls within the spirit and scope of the present invention, as defined by the appended claims. Preferably, the weak spot is positioned centrically between the two tabs. By means of the embodiment according to the present disclosure, a well-balanced connection could be maintained which assures a smooth action of the interaction partners.

In addition, it is advantageous when the connecting region at the proximal end of the base body has at least two tabs which are arranged one after another in an axial direction of the base body. Moreover, the two tabs could have the same circumferential length or different lengths. Further, an axial distance of the tabs is matched to the width of the corresponding fitting partner or the threaded part of the male Luer fitting, respectively. Thus, the threaded connection between the coupling and the upstream component could be performed tightly and safely.

Further, providing at least one valve, which is positioned at the distal end of the base body, allows advantageously controlling a passage of media, like, for example, fluids, agents and/or medical devices through the coupling. Preferably, the valve is embodied as hemostatic and/or splittable or slittable valve. In another embodiment of the present disclosure, it is provided that the valve is embodied as a one-way valve, whereby an infusion of agents into the body could be allowed, but leakage of blood could be favourably precluded. Moreover, it is also provided that the valve could be embodied as a bidirectional valve, wherein the flow of media is beneficially precluded in either direction through the valve. Infusion and/or aspiration could preferably take place trough a cannula adapted to pass through the valve. Generally, it is also possible that the valve is embodied as an adjustable, compression, or syringe activated valve and/or as any other valve being feasible for a person skilled in the art.

Advantageously, the at least one valve is positioned distally with respect to the recess. Thus, the connecting region for the applicator is unaffected by the valve. Consequently, the connection function and the valve function could be arranged separately but at the same time positioned adjacent to each other. This, in turn, results in a space saving arrangement.

Furthermore, it can be advantageous when the base body is integrally formed with the delivery device. In this context "integrally formed" as used herein is intended to mean, in particular, that the base body and the delivery device are molded out of one piece and/or that the base body and the delivery device could only be separate with loss of function for one of the parts. By means of the embodiment according to the present disclosure, resources, costs and assembly efforts can be reduced profitably.

A good manageability can be achieved when the coupling has a handle which is attached to the base body. The handle is advantageously attached at the area between the connecting regions at the proximal and distal ends of the base body and/or integrally formed with the coupling. Moreover, it is embodied as a loop, whereby the handling could be increased and optimized.

Thus, the present disclosure provides desirably a single device that enables easy manipulation of the position and the infusion of diagnostic and/or therapeutic agents and which is subsequently capable of delivering, for example, a pacing lead and being removed by slitting or splitting.

Various other objects, aspects and advantages of the present invention can be obtained from a study of the specification, the drawings, and the appended claims.

BRIEF DESCRIPTION OF THE DRAWINGS

The present disclosure is explained in the following in greater detail, as an example, with reference to an embodiment depicted in drawings. They show:

FIG. 8 shows a schematic view of a Luer connection of the coupling from FIG. 4;

FIG. 11 shows a fifth embodiment of a coupling with a one-way valve;

FIG. 12 shows a sixth embodiment of a coupling with a bidirectional valve;

DETAILED DESCRIPTION OF THE INVENTION

Figure 9:
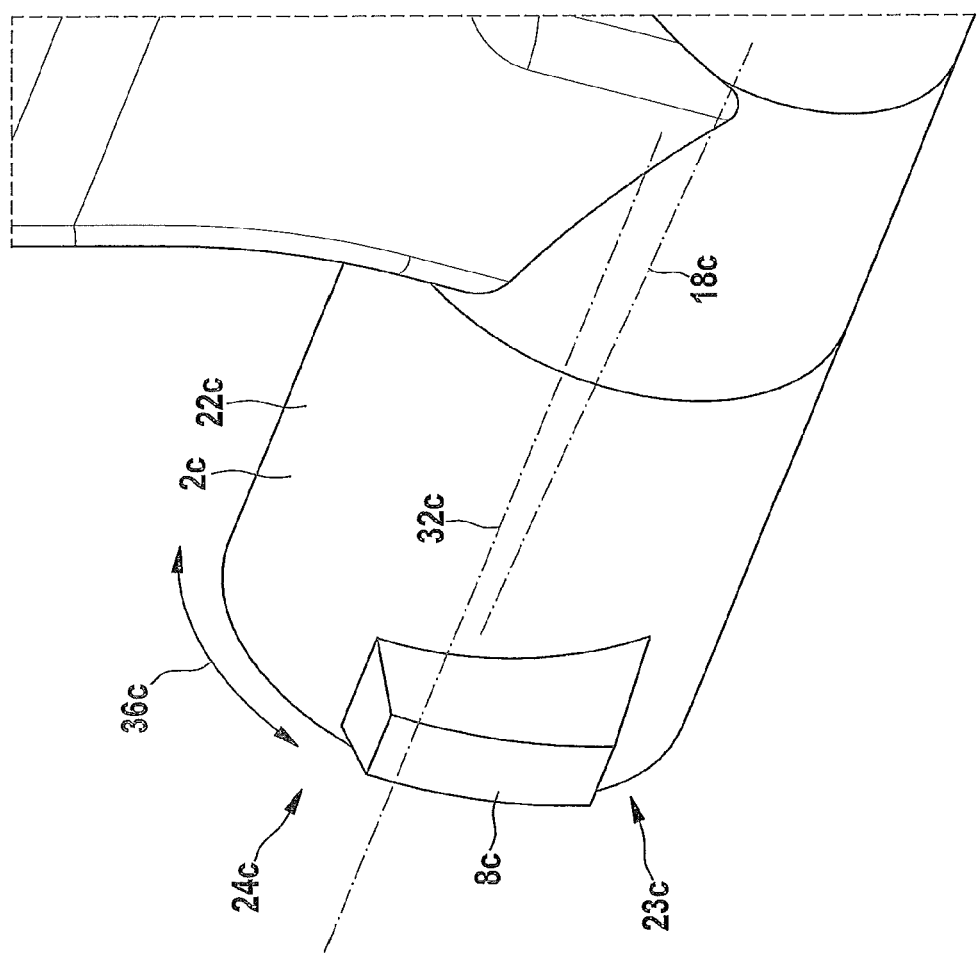
FIG. 9 shows a third embodiment of a coupling with a size reduced tab.
Figure 10:
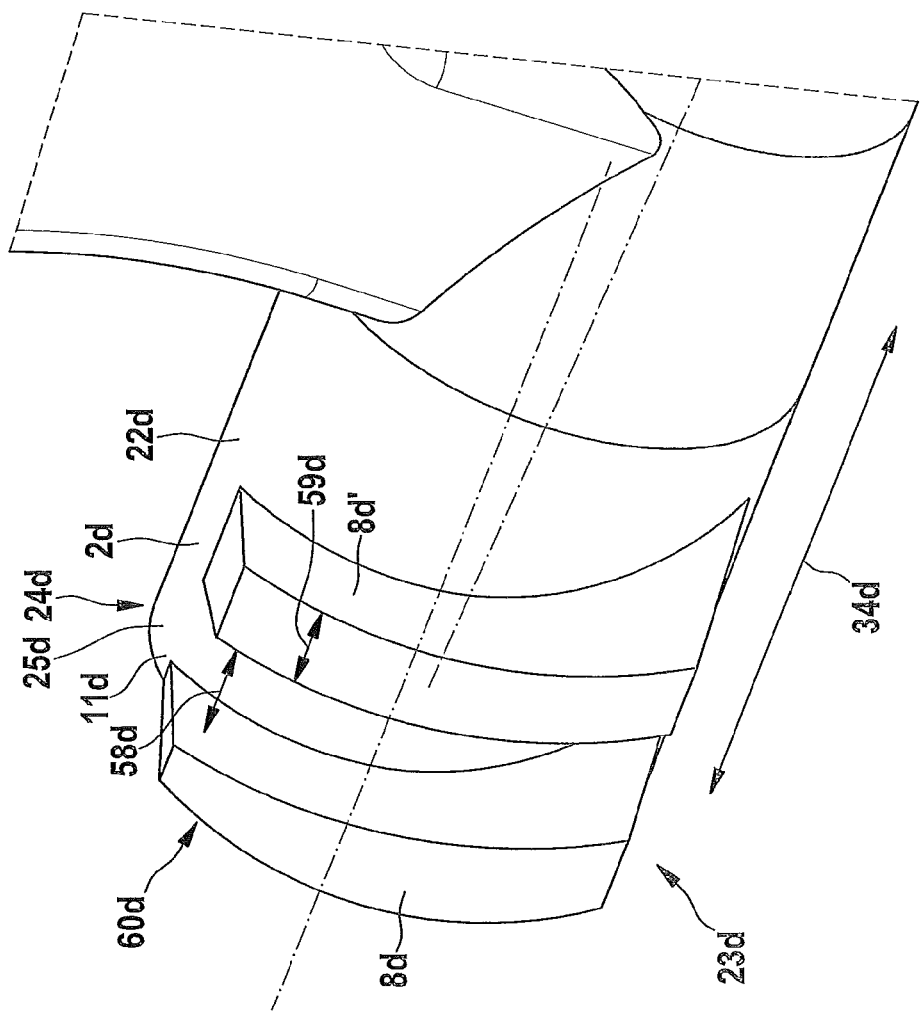
FIG. 10 shows a forth embodiment of a coupling with to axially arranged tabs.

Elements that are functionally identical or similar-acting are labelled using the same reference numerals in the figures. The figures are schematic depictions of the present invention. They do not depict specific parameters of the present invention. Furthermore, the figures merely show typical embodiments of the present invention and should not limit the present invention to the embodiments shown. To distinguish between the various embodiments, the letters "a" to "i" have been added to the reference characters of the figures as used in the specification. Specifically, FIGS. 1-3 include the letter "a". FIGS. 4-8 include the letter "b". FIG. 9 includes the letter "c". FIG. 10 includes the letter "d". FIG. 11 includes the letter "e". FIG. 12 includes the letter "f". FIG. 13 includes the letter "g". FIG. 14 includes the letter "h". FIG. 15 includes the letter "i".

Regarding elements in a figure that are not described further, reference is made to the respective description of the elements in preceding figures to avoid unnecessary repetition.

Figure 1:
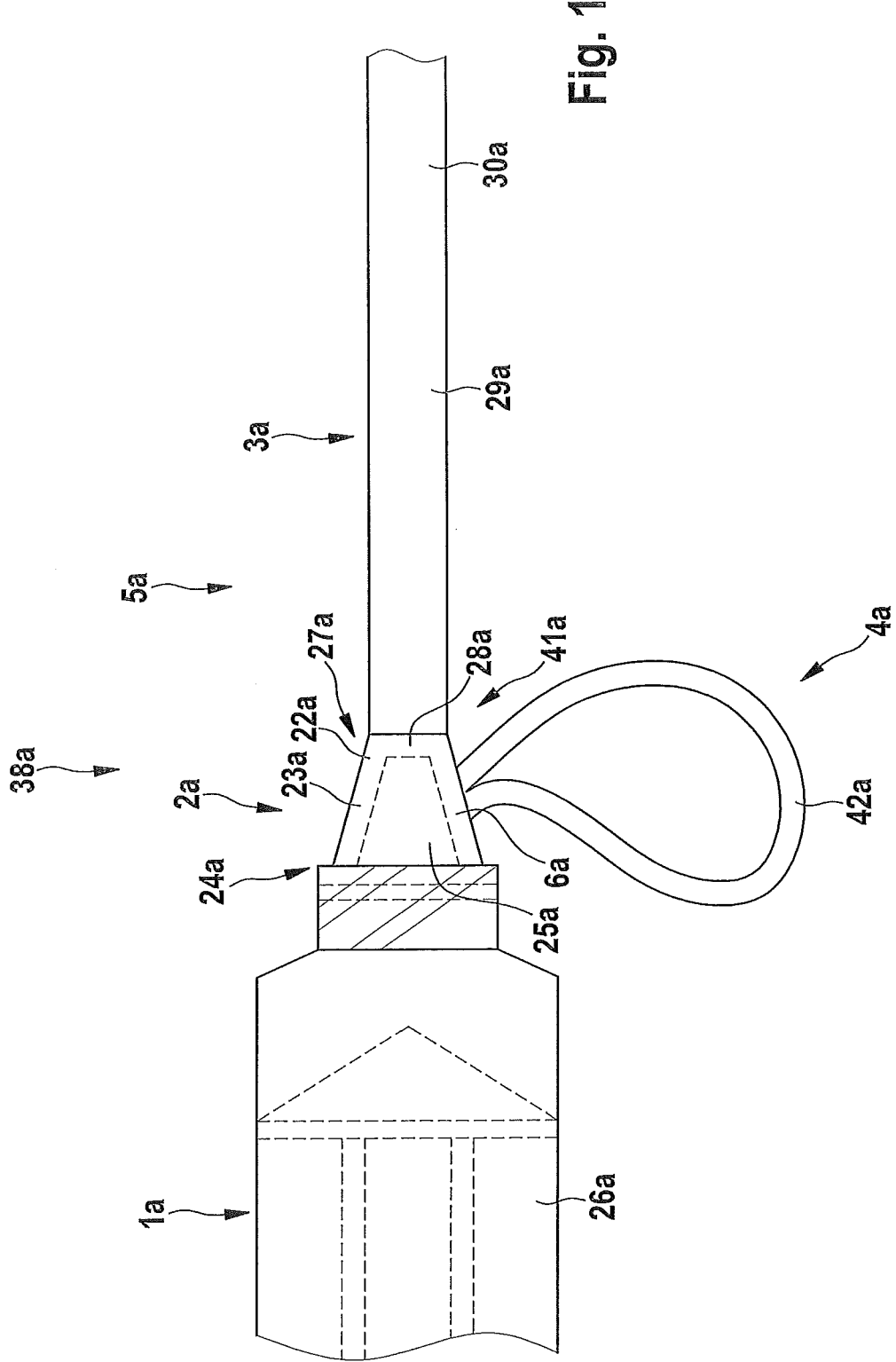
FIG. 1 shows a coupling according to the present disclosure attached to a Luer fitting of a syringe in a side view.

FIG. 1 shows an apparatus 38a which is intended for delivering a medical device 31a, like a lead 7a, and an agent 39a, like a radiocontrast, (see FIG. 2) during a vascular procedure, to a target location and into a human's body lumen or a vasculature, respectively (not shown). The apparatus 38a includes an applicator 26a, embodied as a syringe 1a, a coupling 22a, embodied as a hub 2a, and a delivery device 29a with a tubular member 30a, embodied as a delivery shaft 3a.

Figure 2:
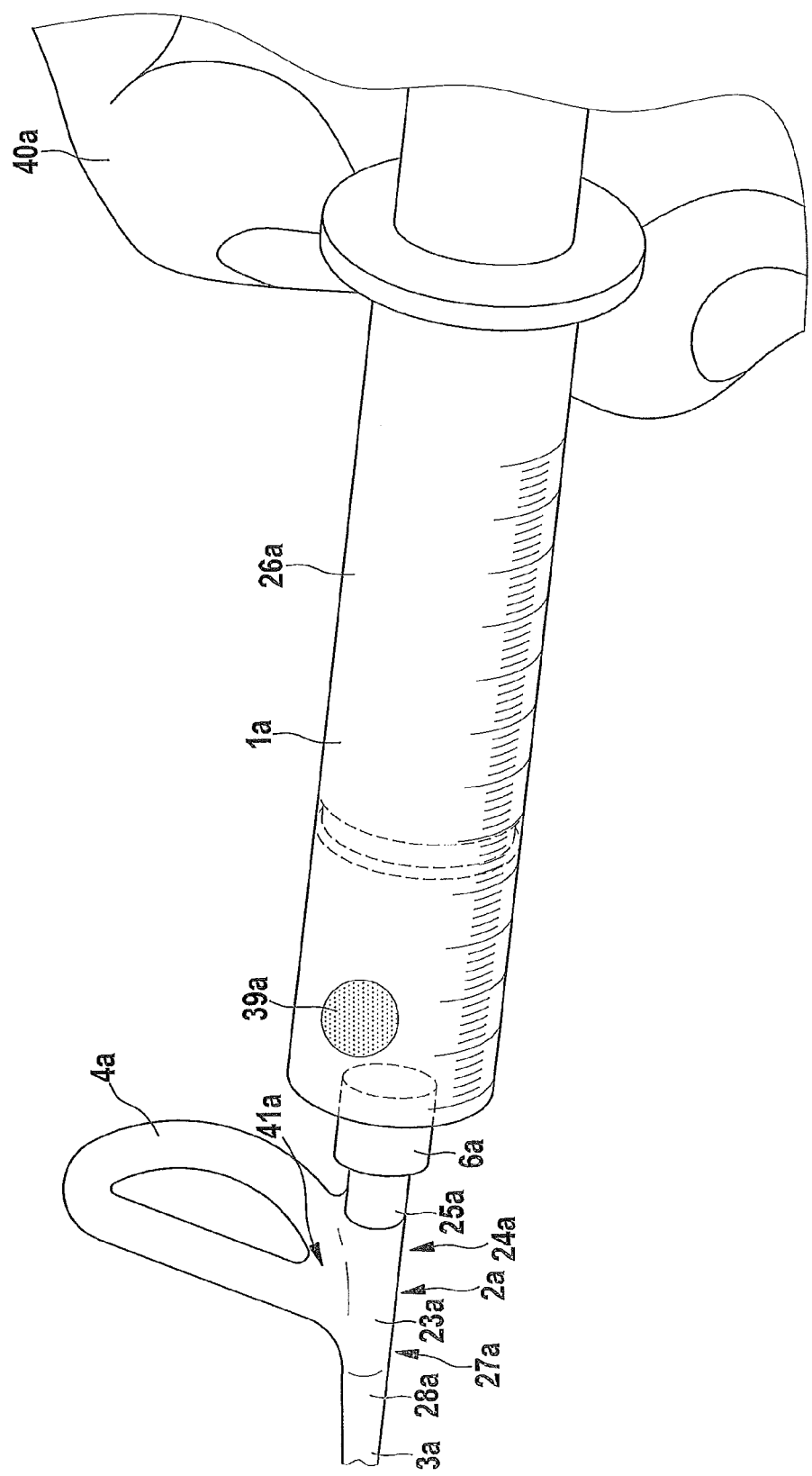
FIG. 2 shows the coupling from FIG. 1 with the syringe.

The coupling 22a has a base body 23a with a proximal end 24a and a distal end 27a, wherein the proximal end 24a is oriented towards an operator 40a (see FIG. 2). Moreover, the base body 23a has a recess 9a, which extends between the proximal end 24a and the distal end 27a and presents a through hole. The distal end 27a is embodied as a connecting region 28a for the delivery device 29a, wherein the connecting region 28a and thus the base body 23a, respectively, is integrally formed with the delivery device 29a. Therefore, a delivery sheath 5a is made up of the shaft 3a and the hub 2a. The proximal end 24a is embodied as a connecting region 25a for the applicator 26a. The hub 2a is adapted to accept a male Luer fitting 6a of the Luer lock syringe 1a or other device (not shown) including a male Luer fitting. Therefore, the connecting region 25a at the proximal end 24a of the base body 23a has a Luer fitting 6a, which is realized by a friction fit of the male Luer fitting 6a of the syringe 1a in the recess 9a of the base body 23a.

The coupling 22a or the hub 2a, respectively, further includes a handle 4a which is attached to or integrally formed with the base body 23a in a region 41a located axially between the connecting regions 25a, 28a. The handle 4a is embodied as a loop 42a and may be used to manipulate the delivery sheath 5a, for example, during removal from the body by means of slitting or splitting.

FIG. 2 illustrates use of such a delivery sheath 5a wherein a Luer lock syringe 1a is connected to the hub 2a of the delivery sheath 5a. The Luer lock syringe 1a can be held in one hand of the operator 40a allowing simultaneous advancement or retraction, rotation, and/or infusion agent 39a or aspiration of blood.

Figure 3:
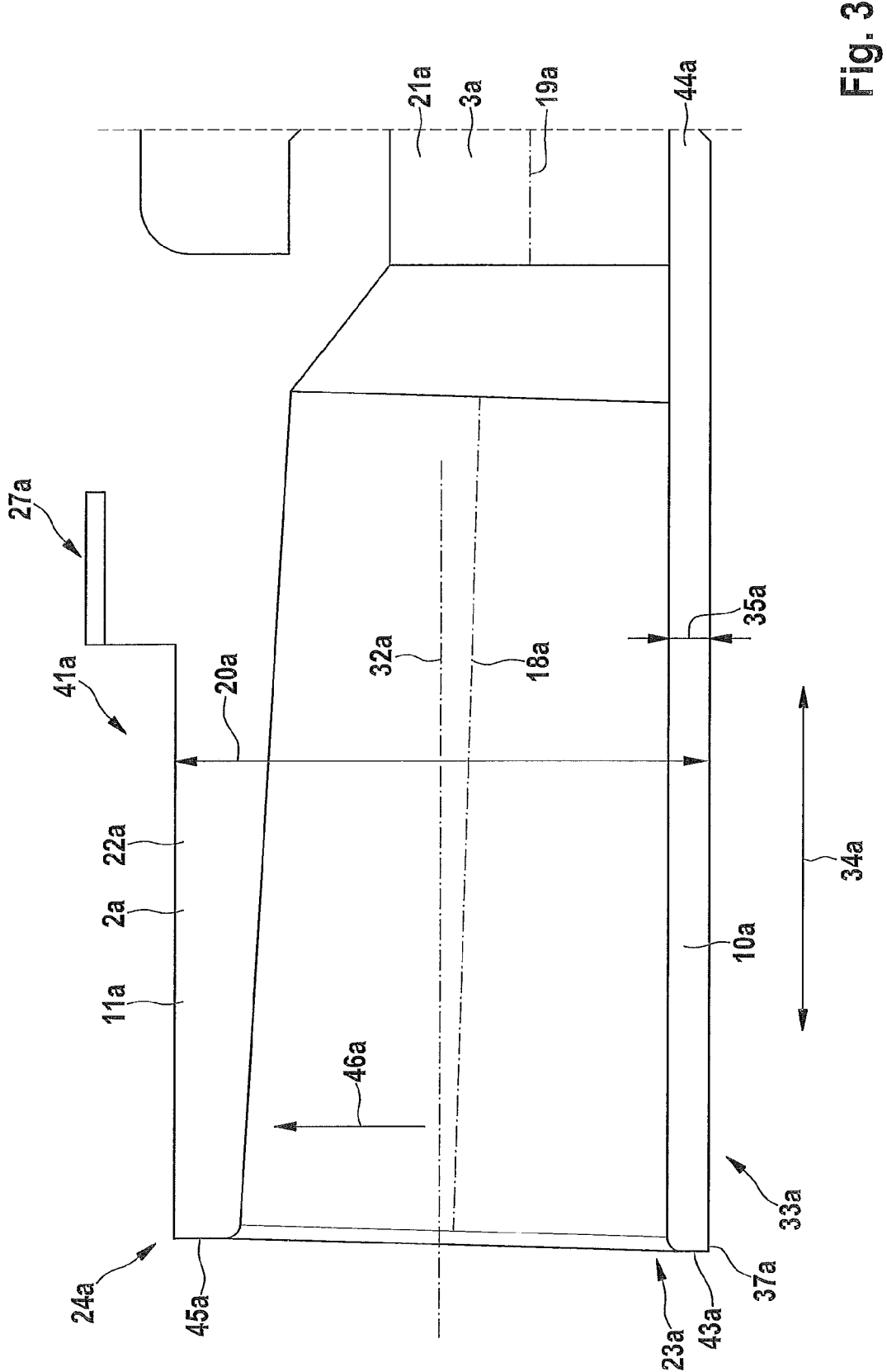
FIG. 3 shows a cross section through the coupling from FIG. 1.

FIG. 3 exemplifies a cross-section through the hub 2a along the image plane in FIG. 1. The hub 2a includes the recess 9a capable of accepting a male Luer fitting 6a of the syringe 1a. The recess 9a may comply with standards describing Luer fittings or may be modified. In this embodiment, the recess 9a is positioned in the hub 2a such that the base body 23a has a weak spot 33a which extends in axial direction 34a of the whole axial extension of the base body 23a and is intended for splitting or slitting of the base body 23a with a tool for splitting or slitting, like, for example, a cutter (not shown). The weak spot 33a is embodied as a first or a thin wall segment 10a having a uniform width 35a in axial direction 34a over the whole axial extension of the base body 23a. Thus, the wall segment 10a of the hub 2a is substantially straight and/or has a substantially uniform thickness for ease of slitting. The slitting wall segment 10a may be relatively thin, for example, compared to a second wall segment or the remaining wall segments of the hub 2a, likewise to facilitate easy slitting. The thin wall segment 10a abuts the recess 9a at least over a segment 43a of a circumference 37a of the recess 9a (not shown in detail; refer to FIG. 6). Also for easy slitting a downstream wall 44a of the delivery shaft 3a has the same width as the thin wall segment 10a.

With respect to the thin wall segment 10a, a thicker wall segment 11a is positioned diametrical opposite to the thin wall segment 10a. The thicker wall segment 11a abuts the recess 9a at least over a segment 45a of the circumference 37a of the recess 9a (not shown in detail; refer to FIG. 6) and extends continuously in a radial direction 46a along the axial direction 34a from the proximal end 24a to the distal end 27a of the base body 23a. Thus, the thicker wall segment 11a provides a structural support for the base body 23a. Therefore, the thin wall segment 10a is, at the proximal end 24a, about two times thinner than the thicker wall segment 11a and, at a region towards the distal end 27a, about three times thinner. Due to this and in order to facilitate slitting, a central axis 18a of the recess 9a is nonparallel with respect to a central axis 32a of the outer diameter 20a of the base body 23a or the hub 2a, respectively, and/or to the central axis 19a of the hub's 2a distal segment and/or the catheter shaft (not shown). In addition to the structural support of the nonparallel axes, they also accommodate Luer taper while maintaining the consistently thin slitting wall segment 10a.

Additionally, the recess 9a is not concentric with the outer diameter 20a of the hub 2a and/or with the distal lumen 21a of the hub 2a or catheter shaft (not shown). In other words, the recess 9a is positioned eccentrically from the outer diameter 20a of the base body 23a, wherein the outer diameter 20a refers to the region 41a located axially between the connecting regions 25a, 28a.

During a vascular procedure, the delivery sheath 5a or the delivery shaft 3a, respectively, with the introduced pacing lead is introduced into the right atrium to deliver the lead to the heart. A position of the delivery sheath 5a within the heart may be manipulated with the handle 4a or the syringe 1a by the operator 40a. Additionally, radiocontrast may be infused in order to identify and/or cannulate the coronary sinus and/or its tributaries. After the exact positioning of the electrodes and the lead 7a and the delivery sheath 5a with the coupling 22a, the delivery shaft 3a will be slit and the delivery sheath 5a will be removed leaving the pacing lead in place. Alternatively, the delivery sheath 5a, including hub 2a may be splittable (e.g., may be pealed away without the aid of a slitter or cutter) to facilitate its removal while leaving the lead in place.

In FIGS. 4 to 15C, eight alternative embodiments of the coupling 22a are shown. Components, features and functions that remain identical are in principle substantially denoted by the same reference characters. To distinguish between the embodiments, however, the letters "a" to "i" have been added to the reference characters of the embodiments, as previously noted. The following description is confined substantially to the differences from the embodiment in FIGS. 1-3, wherein with regard to components, features and functions that remain identical, reference may be made to the description of the embodiment in FIGS. 1-3.

Figure 4:
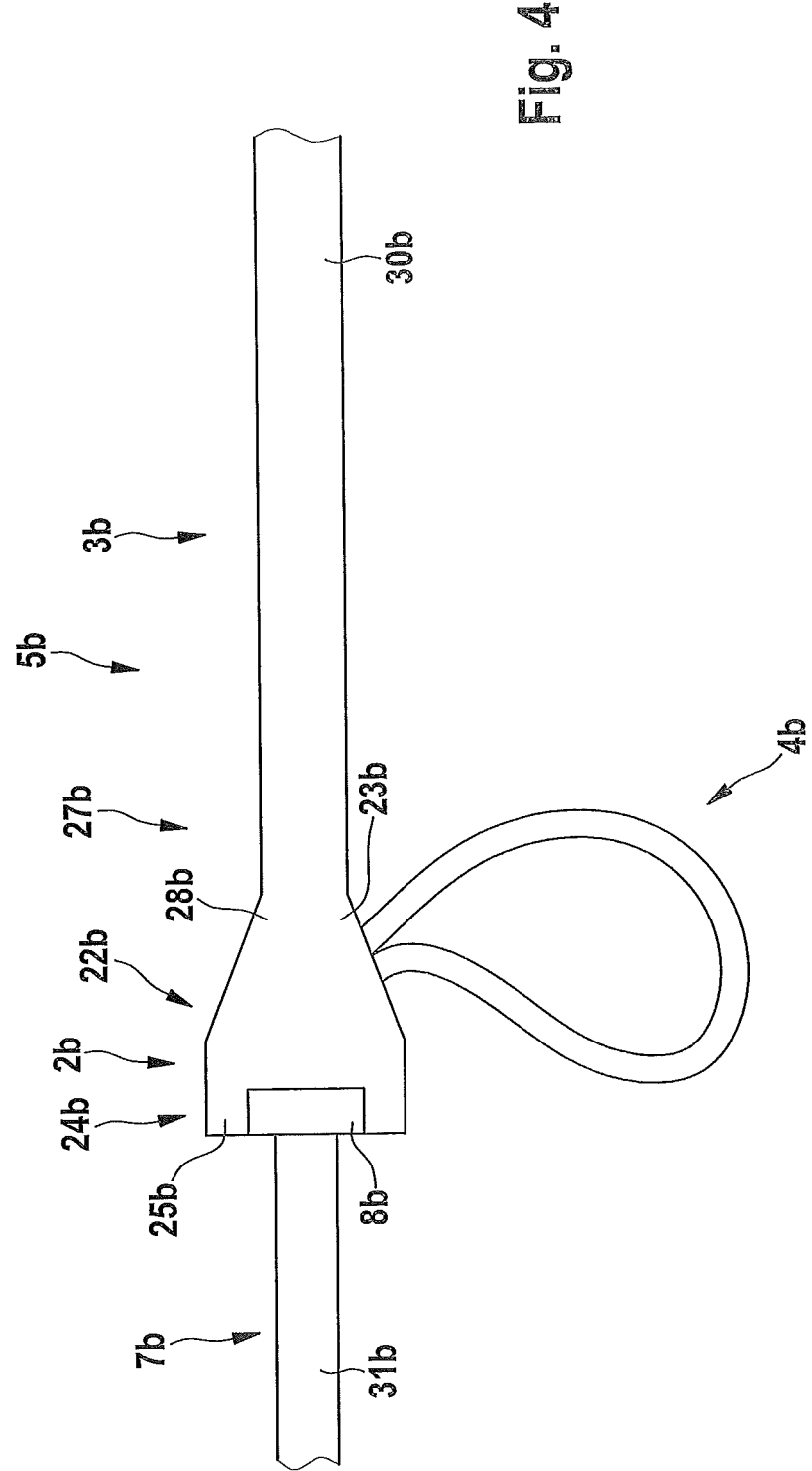
FIG. 4 shows an alternative embodiment of a coupling with a partly inserted lead.

FIG. 4 illustrates an alternative embodiment of a delivery sheath 5b after removal of a Luer lock syringe (not shown). The delivery sheath 5b has a coupling 22b or hub 2b, respectively, with a base body 23b and a tubular member 30b or delivery shaft 3b arranged at a connecting region 28b of a distal end 25b of the base body 23b. Thus, the delivery device 29b and the base body 23b are integrally formed with each other. A medical device 31b or a pacing lead 7b is now inserted through the hub 2b of the delivery sheath 5b. A connecting region 25b at a proximal end 24b of the base body 23a has connecting means embodied as tabs 8b, which extend in a circumferential direction 36b of the base body 23b. Only one tab 8b for engaging a threaded Luer lock fitting, specifically a male Luer fitting 6b, of the syringe 1b is shown in FIG. 4 (see FIG. 8 for both). After delivery of the lead 7b, the delivery sheath 5b including hub 2b may be slit using a slitter (not shown) in order to remove the delivery sheath 5b from the body while leaving the lead 7b in place. Alternatively, the delivery sheath 5b, including hub 2b may be splittable (e.g., may be pealed away without the aid of a slitter or cutter) to facilitate its removal while leaving the lead 7b in place. The hub 2b or the base body 23b has a least a weak spot 33b embodied as a thin wall segment 10b to facilitate splitting (see FIG. 6). Alternatively, a score line or other means to facilitate splitting are feasible and are within the spirit and scope of the present invention. The weak spot 33b or the thin wall segment 10b extends in axial direction 34b of the base body 23b and has a uniform width 35b in axial direction 34b of the base body 23b (not shown).

Figure 5:
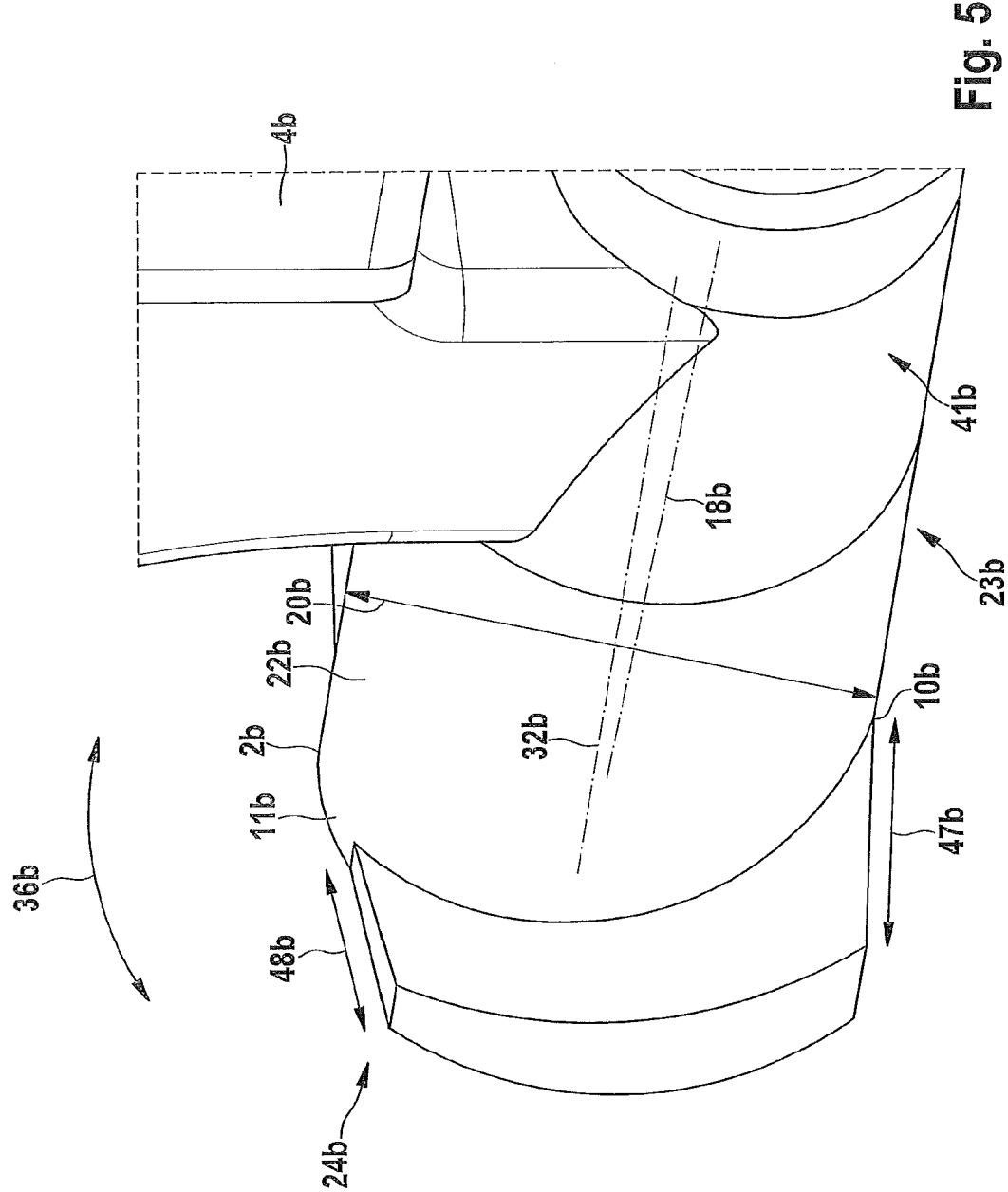
FIG. 5 shows a perspective side view of the coupling from FIG. 4.

FIG. 5 is a perspective side view of the hub 2b including one tab 8b arranged at the proximal end 24b. A reach 47b of the tab 8b which extends from the side where the thin wall segment 10b is located is longer than a reach 48b which extends from a wall segment 11b which is arranged opposite to the thin wall segment 10b. Basically, one tab 8b would be sufficient for the Luer fitting. In a region 41b located between the ends 24b, 27b a handle 4b is molded to the base body 23b.

Figure 6:
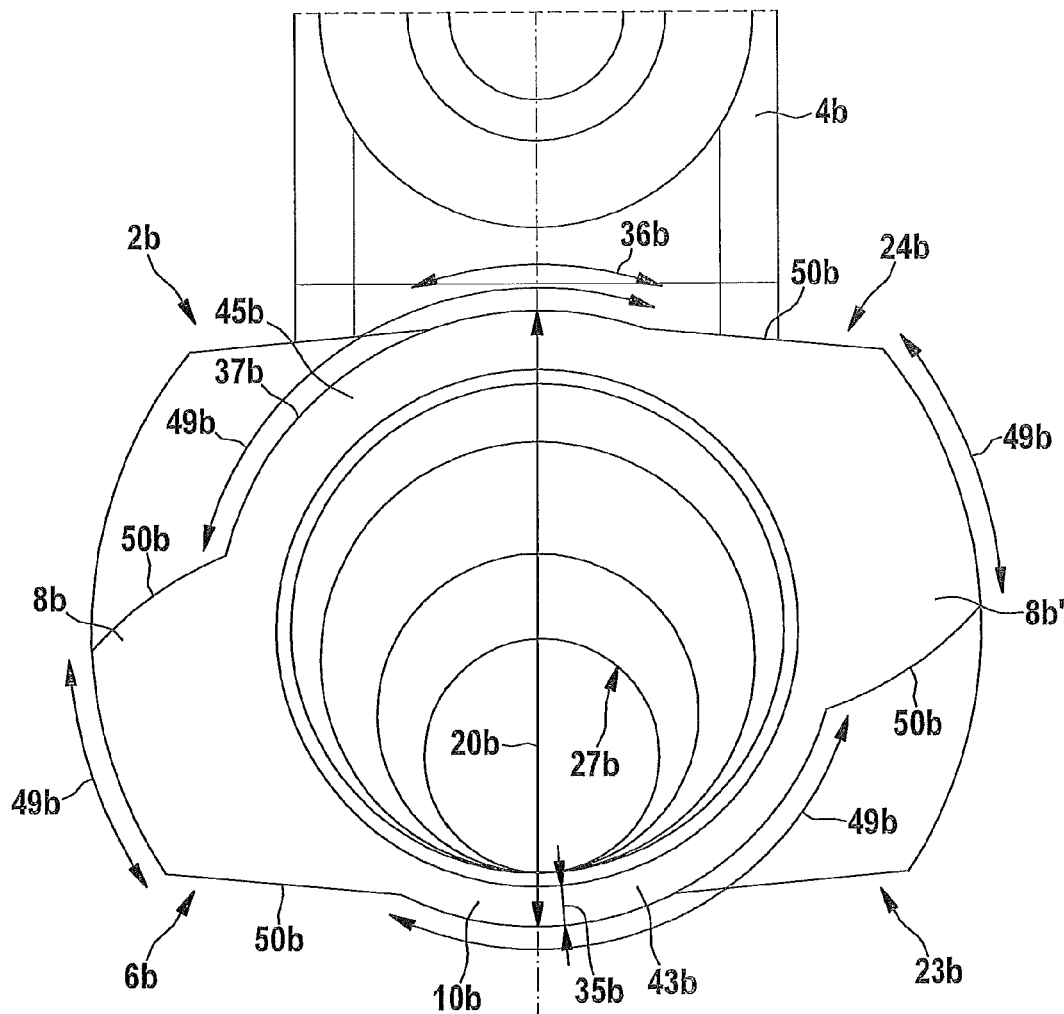
FIG. 6 shows a top view from a proximal end of the coupling from FIG. 4.

FIG. 6 is a view from the back of the hub 2b looking into a recess 9b or a top view of the proximal end 24b. The recess 9b extending between the proximal end 24b and the distal end 27b is positioned eccentrically from an outer diameter 20b of the base body 23b (see FIG. 7a) and a central axis 18b of the recess 9b is nonparallel in respect to a central axis 32b of the outer diameter 20b of the base body 23b (see also FIG. 5). The thin slitting wall segment 10b is seen below. A thicker wall segment 11b provides structural support to the hub 2b and is positioned diametrical opposite to the thin wall segment 10b. The thin wall segment 10b and the thicker wall segment 11b are segments 43b, 45b which have roughly the same circumferential length 49b which is about a fourth of the circumference 37b, or about 90°.

The hub 2b further includes two tabs 8b adapted to engage the Luer lock syringe or other threaded Luer adapter (not shown). As depicted, the threads or tabs 8b, 8b' extend over a part of an outer circumference 37b of the base body 23b or only partially around the circumference 37b of the proximal end 24b of the hub 2b so that the thin slitting wall segment 10b remains accessible for slitting. Moreover, the two tabs 8b, 8b' are positioned diametrical towards each other and have roughly the same circumferential length 49b which is about a fourth of the circumference 37b, or about 90°. Furthermore, surfaces 50b of the tabs 8b, 8b' which face in circumferential direction 36b are embodied as rounded down to lighten the engagement of the tabs 8b, 8b', which function as female Luer fitting 6b', with the male Luer fitting 6b. The general features of the tabs 8b, 8b' could also be applicable to the following embodiments in FIGS. 9, 10, 11, 13 and 15A-15C. In principle, the tab/luer thread could extend about 270°, omitting only the thin slitting wall segment. In this particular design, there is an additional break in the tab opposite the thin slitting wall segment to provide clearance for installation of a screw which is used in this specific design.

Figure 7B:
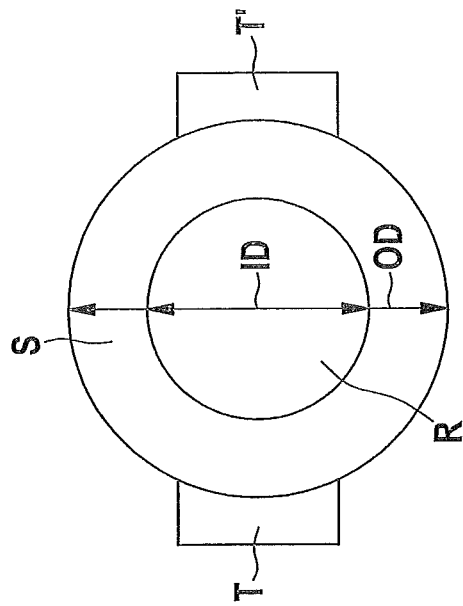
FIG. 7B shows a schematic top view from a proximal end of a coupling according to the state of the art.
Figure 7A:
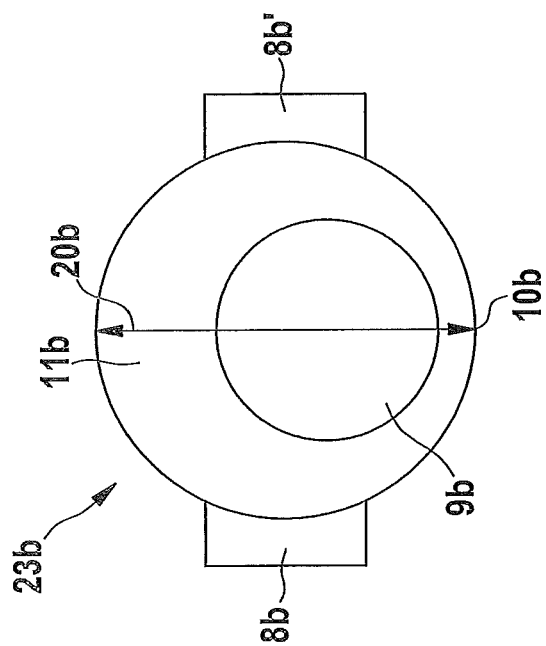
FIG. 7A shows a schematic top view from a proximal end of the coupling from FIG. 4.

FIGS. 7 and 8 further describe the positional relationship of the recess (which is a female Luer fitting 6b') with respect to the threads/tabs 8b, 8b' and the outer diameter 20b of the hub 2b in order to facilitate slitting. FIG. 7A shows the eccentric arrangement of the recess 9b in respect to the outer diameter 20b of the base body 23b. Due to this, the thin wall segment 10b could be realized. In FIG. 7B an arrangement according to a standard or state of the art device is shown. A recess R is arranged centrically in respect to an outer diameter OD, thus an inner diameter ID and the outer diameter OD are concentrically, both for simplicity of design as well as for flexibility in a location of threads or tabs T, T'. However, this results in a thick wall section S that is difficult to slit.

FIG. 8 shows the female Luer fitting 6b' with the tabs 8b, 8b' of the base body 23b engaged in a male Luer fitting 6b of a syringe 1b. As the sealing surface of a Luer is only between an inner diameter 51b of the female Luer fitting 6b' or the recess 9b, respectively, and an outer diameter 52b of the male Luer (and not between an outer diameters 53b, 20b of the threads/tab 8b, 8b' and the base body 23b, respectively, of the female Luer fitting 6b' and an inner diameter 54b of a thread 55b of the male Luer fitting 6b), the Luer may still be constructed eccentrically such that the threads/tabs 8b, 8b' are concentric with the inner diameter 51b of the recess 9b, but not with the outer diameter 20b of the base body 23b. Thus, the threads/tabs 8b, 8b' will fit clearly within the thread 55b of the male Luer lock fitting 6b or syringe 1b and seal on the inner diameter 51b of the female Luer fitting 6b' even while leaving a gap 56b on the outside or between the circumference 37b of the base body 23b and the thread 55b of the male Luer filling 6b.

Thus, outer contour 57b of the male Luer fitting 6b is concentric with the inner diameter 52b of the male Luer fitting 6b and with the outer diameter 52b of the male Luer fitting 6b and the inner diameter 51b of the female Luer fitting 6b', respectively, through center A. The outer diameter 20b of the base body 23b is not concentric with outer contour 57b of the male Luer fitting 6b or the inner diameter 51b of the female Luer fitting 6b' and with the outer diameter 52b of the male Luer fitting 6b, but has its own center at B which is opposite the thin wall segment 10b or the slitting side.

FIG. 9 illustrates a variation of the tab 8b that may be used for securing a threaded Luer adapter (not shown) to a coupling 22c or a hub 2c. The tab 8c is with respect to the Luer according to FIG. 5 reduced in its size in circumferential direction 36c of a base body 23c. Generally, more than one tab 8c could be practicable.

FIG. 10 illustrates a further variation on tabs 8b, 8c that may be used for securing a threaded Luer adapter (not shown) to a coupling 22d or a hub 2d. A connecting region 25d at a proximal end 24d of a base body 23d has at least two tabs 8d, 8d' which are arranged one after another in axial direction 34d of the base body 23d. Further, an axial distance 58d of the tabs 8d, 8d' is matched to the width of the corresponding male Luer fitting (not shown). In this embodiment, the distance 58d is equal to the axial extension 59d of one tab 8d, 8d'. Moreover, the tabs 8d, 8d' have the same axial and circumferential lengths. The proximal tab 8d may have a tapered tip 60d in the region of a thicker wall 11d to facilitate the engagement of the Luer connection. In general, more than two axially arranged tab 8d, 8d' could be feasible. Also an arrangement of another duplex of tabs 8d, 8d' with is positioned diametrical towards the first duplex is possible.

In further embodiments (not shown), the hub may be adapted with alternative means for attaching to a syringe or other device (not shown). For example, a syringe (not shown) and the hub may each be adapted with a snap fitting or other means (other than a threaded Luer fitting) for attaching to each other and enabling the hub to be manipulated by means of the syringe (not shown). Further, alternatively, the tab(s) may be omitted altogether, and the friction fit of male Luer fitting (not shown) in the recess (as shown in FIG. 3) may be sufficient to enable the hub to be manipulated by means of its attachment to a syringe (not shown).

FIG. 11 illustrates a further alternative embodiment of a coupling 22e or hub 2e, respectively, which is a part of a delivery sheath 5e with a delivery device 29e or a tubular member 30 embodied as a delivery shaft 3e for delivering a medical device (not shown). The coupling 22e has a base body 23e with a recess 9e extending between a proximal end 24e and a distal end 27e of the base body 23e. Moreover, the recess 9e is positioned eccentrically from an outer diameter 20e of the base body 23e and a central axis 18e of the recess 9e is nonparallel in respect to a central axis 32e of the outer diameter 20e of the base body 23e. The hub 2e further comprises a slittable hemostatic valve 12e, which is positioned at the distal end 27e of the base body 23e. The valve 12e is positioned distally to the recess 9e and is embodied as a one way valve, e.g., allowing infusion of agents into the body, but precluding leakage of blood (not shown). Tabs positioned at the proximal end 24e for connecting the hub 2e to a syringe are possible, but not shown.

FIG. 12 illustrates a further alternative embodiment in which a coupling 22f or a hub 2f comprises a bidirectional valve 12f such that flow is precluded in either direction through the valve 12f. A syringe 1f further comprises a cannula 13f adapted to pass through the valve 12f when a distal end 61f of the syringe 1f is engaged in the recess 9f. Infusion and/or aspiration can take place through the valve 12f by way of the cannula 13f when it is crossing the valve 12f. However, when the cannula 13f is removed from the valve 12f, no flow is permitted. A compression, or syringe activated valve (not shown) may also be used.

Figure 13A:
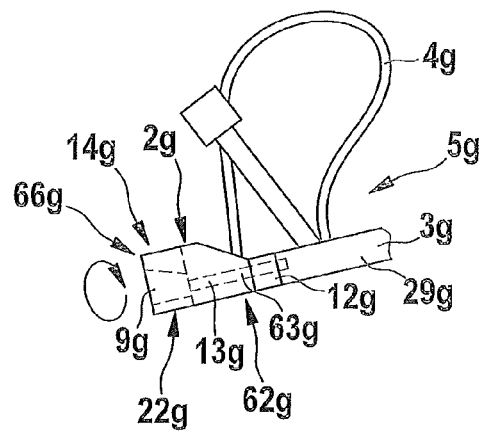
FIG. 13A shows a side view of a seventh embodiment of a coupling embodied as a bypass tool.

FIG. 13A illustrates a further alternative embodiment of a coupling 22g or a hub 2g which could be connected to a connecting region 62g of a delivery sheath 5g with a delivery device 29g or a delivery shaft 3g (for clearness connecting region 62g is not shown true to original in FIG. 13A). Because syringes generally do not have a cannula such as could be used to bypass a bidirectional valve 12g, or alternatively a one-way valve with a small through hole, a separate bypass tool 14g may be provided to adapt a syringe with a cannula to bypass the valve 12g. The bypass tool 14g would be removed along with the syringe prior to slitting. In this embodiment, the coupling 22g is embodied as a bypass tool 14g and comprises a recess 9g for receiving the syringe or other male Luer fitting (not shown) and a cannula 13g or a bypass sheath 63g adapted to pass through the valve 12g. The bypass tool 14g may be secured against longitudinal movement by friction between the bypass sheath 63g and the hemostatic valve 12g. Also, a side port of the delivery sheath 5g and a handle 4g is shown.

Figure 13B:
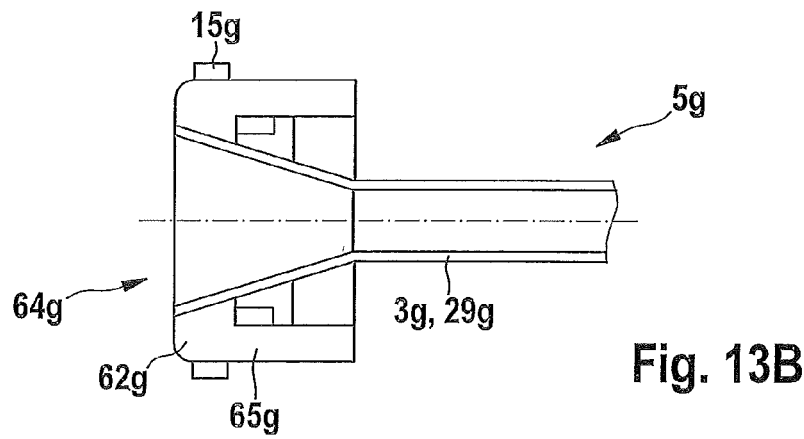
FIG. 13B shows a proximal end of a delivery sheath embodied as connecting region for the coupling of FIG. 13A.
Figure 13C:
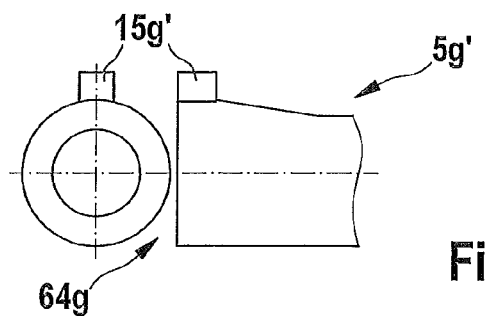
FIG. 13C shows an alternative proximal end with only one pin in a top and a side view.

FIG. 13B depicts in more detail an embodiment of the connection region 62g of a proximal end 64g of the delivery sheath 5g with attachment means 15g (valve 12g not shown). The connection region 62g, which could also function as a handle, is embodied as a cap 65g with outer pins 15g for the connection with the coupling 22g or a proximal end 66g of the bypass tool 14g, respectively. An alternative embodiment of a proximal end 64g' of an deliver sheath 5g' with only one pin 15g' is shown in FIG. 13C.

Figure 13D:
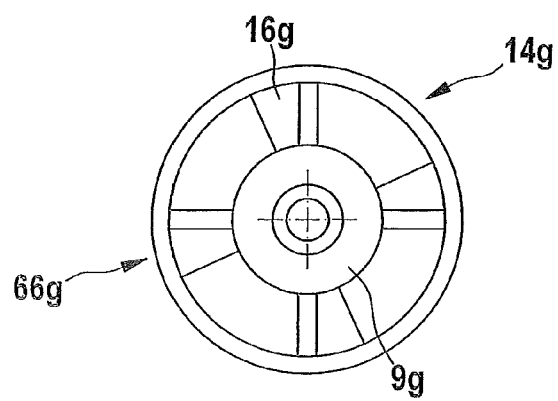
FIG. 13D shows an end-on view looking into a recess of the coupling from FIG. 13A with an attachment means.

In FIG. 13D, an end-on view looking into the recess 9g of the bypass tool 14g is shown. As an example, a snap fitting may facilitate the connection of the bypass tool 14g to the connecting region 62g of the delivery sheath 5g. The bypass tool 14g has at its proximal end 66g an attachment means 16g for attaching the bypass tool 14g to the connecting region 62g and which is adapted to engage a corresponding feature or pins 15g, respectively, on the delivery sheath 5g. For example, the bypass tool 14g may have a twist-lock mechanism 16g adapted to engage one or more features 15g on the proximal end 63g of the delivery sheath 5g. The attachment means 16g may have an inner knurl or structure (not shown) to lock on one or more pins 15g, located at the proximal end 64g of the delivery sheath 5g. Alternatively, or in addition to, it is possible that the proximal end 66g of the bypass tool 14g further has an outer structure for locking on a syringe (not shown). The bypass tool 14g and the syringe may be secured against longitudinal movement by locking on the handle's pin 15g and by friction between bypass sheath 63g and the hemostatic valve 12g. The bypass tool 14g and the syringe may be secured against axial movement by locking on the handle's pin 15g.

Figure 14A:
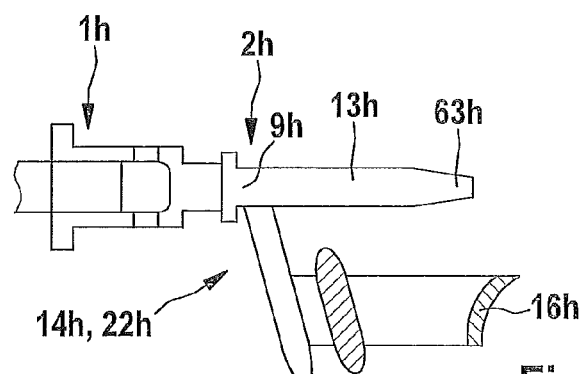
FIG. 14A shows a side view of an eighth embodiment of a coupling connected to a syringe embodied as a bypass tool with an attachment means.
Figure 14B:
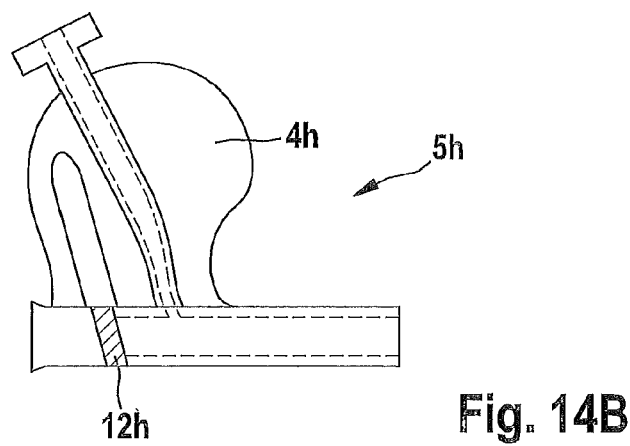
FIG. 14B shows a delivery sheath with a connecting region for the coupling from FIG. 14A.
Figure 14C:
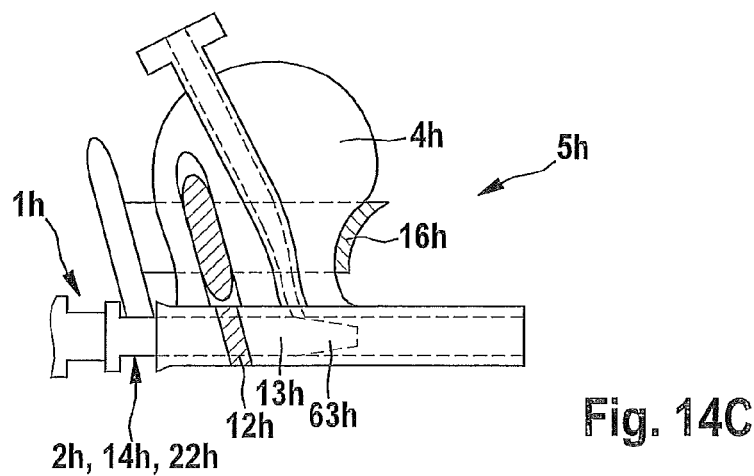
FIG. 14C shows an assembled arrangement of the coupling and the delivery device from FIGS. 14A and 14B.

FIG. 14 illustrates a further alternative embodiment, in which a coupling 22h or hub 2h embodied as a bypass tool 14h comprises a recess 9h for receiving a syringe 1h or other male Luer fitting (not shown) and a cannula 13h or a bypass sheath 63h adapted to pass through a valve 12h (see FIG. 14A). The bypass tool 14h further comprises an attachment means 16h adapted to engage a corresponding feature on a delivery sheath 5h shown in FIG. 14B. For example the bypass tool 14h comprising an attachment means 16h adapted to clip to a handle 4h of the delivery sheath 5h (see FIG. 14C).

Figure 15A:
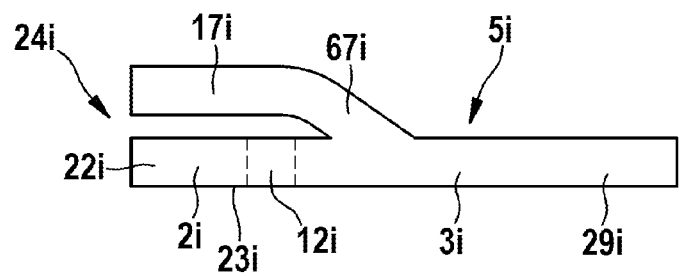
FIG. 15A shows a ninth embodiment of a coupling with a side-port.
Figure 15B:
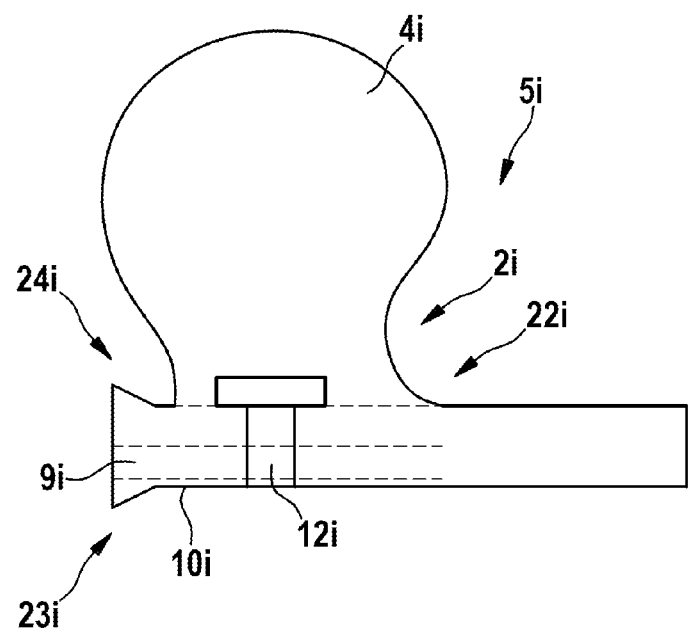
FIG. 15B shows a side view of the coupling from FIG. 15A.
Figure 15C:
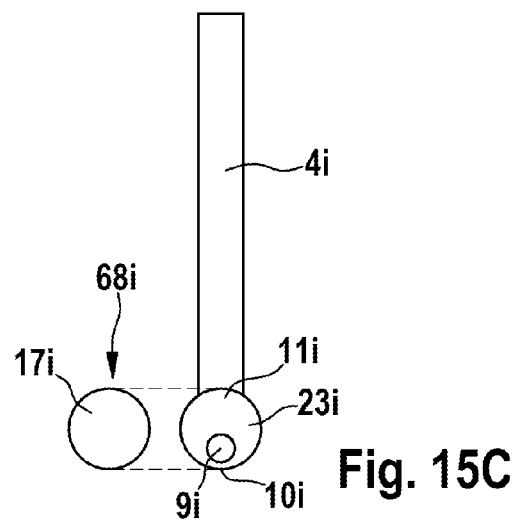
FIG. 15C shows a top view from a proximal end of the coupling from FIG. 15A.

FIGS. 15A to 15C illustrate in a first and a second side view, as well as in a top view from a proximal end 24i, an alternative embodiment where a delivery sheath 5i with a coupling 22i or hub 2i including an in-line side port 17i adapted to receive a syringe (not shown) is depicted. Starting at the proximal end 24i of a base body 23i of the hub 2i, the in-line side port 17i extends in parallel to the base body 23i and discharges with a curved segment 67i into a delivery shaft 3i of the delivery device 29i downstream of a valve 12i which is positioned distally of a recess 9i of the coupling 22i (see FIG. 15A). As could especially be seen in FIG. 15C, the in-line side port 17i is arranged at a side 68i of the base body 23i which is not slit during the procedure and/or which is circumferentially located between a thin wall segment 10i and a thicker wall segment 11i which abut the recess 9i. Tabs located at the proximal end 24i for connecting the hub 2i to the syringe are possible but not shown. The in-line side port 17i may be further adapted with conventional Luer locking mechanisms and does not need to be slit as part of the procedure.

It will be apparent to those skilled in the art that numerous modifications and variations of the described examples and embodiments are possible in light of the above teaching. The disclosed examples and embodiments are presented for purposes of illustration only. The present invention is not confined to the specific details set forth, but includes various changes and modifications that may suggest themselves to those skilled in the art, all falling within the spirit and scope of the present invention as defined by the following claims, which are to be given their full scope and breadth. Therefore, it is the intent to cover all such modifications and alternate embodiments as may come within the true scope of this invention, which is to be given the full breadth thereof. Additionally, the disclosure of a range of values is a disclosure of every numerical value within that range.

REFERENCE NUMERALS

The following reference numerals are used herein to identify the following elements.

1 syringe
2 hub
3 shaft
4 handle
5 sheath
6 Luer fitting
7 lead
8 tab
9 recess
10 segment
11 segment
12 valve
13 cannula
14 bypass
15 feature/pin
16 attachment means
17 side port
18 axis
19 axis
20 diameter
21 lumen
22 coupling
23 base body
24 proximal end
25 connecting region
26 applicator
27 distal end
28 connecting region
29 delivery device
30 tubular member
31 medical device
32 axis
33 weak spot
34 axial direction 35 width
36 circumferential direction
37 outer circumference
38 apparatus
39 agent
40 operator
41 region
42 loop
43 segment
44 wall
45 segment
46 radial direction
47 reach
48 reach
49 circumferential length
50 surface
51 inner diameter recess
52 outer diameter male
53 outer diameter female
54 inner diameter male
55 thread
56 gab
57 contour
58 distance
59 extension
60 tip
61 end
62 connecting region
63 sheath
64 end
65 cap
66 end
67 segment
68 side
A center
B center
ID inner diameter
OD outer diameter
R recess
S wall section
T tab

We claim:

1. A coupling, comprising a hub, with a base body having a proximal end, embodied as a connecting region for an applicator, and a distal end, embodied as connecting region for a delivery device with a tubular member for delivering a medical device into a part of an animal or human body, and having a recess extending between the proximal end and the distal end, wherein the recess comprises a through hole and is positioned eccentrically from an outer diameter of the base body, and wherein a central axis of the recess is nonparallel in respect to a central axis of the outer diameter of the base body;

wherein the base body has at least a weak spot which extends in an axial direction of the base body and is intended for splitting or slitting of the base body with a cutter tool;

wherein the weak spot is embodied as a thin wall segment having a uniform width in the axial direction of the base body;

wherein with respect to the thin wall segment, a thicker wall segment is positioned diametrical opposite to the thin wall segment and wherein the thicker wall segment provides a structural support for the base body, the thicker wall segment having a width that is greater than the width of the thinner wall segment; and wherein the width of the thicker wall segment continuously increases in a radial direction of the recess from the proximal end to the distal end of the base body.

2. The coupling according to claim 1, wherein the connecting region at the proximal end of the base body has at least one Luer fitting.

3. The coupling according to claim 1, wherein the connecting region at the proximal end of the base body has at least one tab extending in a circumferential direction of the base body.

4. The coupling according to claim 1, wherein the connecting region at the proximal end of the base body has at least one tab extending over a part of the outer circumference of the base body.

5. The coupling according to claim 1, wherein the connecting region at the proximal end of the base body has at least two tabs, which are positioned diametrical towards each other and extend over a part of the outer circumference of the base body.

6. The coupling according to claim 1, wherein the connecting region at the proximal end of the base body has at least two tabs which are arranged one after another in an axial direction of the base body.

7. The coupling according to claim 1, wherein at least one valve is positioned at the distal end of the base body.

8. The coupling according to claim 7, wherein the at least one valve is positioned distally with respect to the recess.

9. The coupling according to claim 1, wherein the base body is integrally formed with the delivery device.

10. The coupling according to claim 1, wherein a handle is attached to the base body.

11. A method for introducing a medical device into an animal or human body comprising the steps of:

manipulating a delivery device for the medical device with an applicator, wherein the delivery device is attached to the applicator via a coupling according to claim 1, removing the applicator from the coupling, placing the medical device through the coupling and the delivery device at an implantation side, and slitting the coupling and the delivery device for removal from the animal or human body.

12. The coupling according to claim 1, wherein the thin wall segment and the thicker wall segment have the same circumferential length.

* * * * *